United States Patent
Albrecht et al.

(10) Patent No.: US 7,485,249 B2
(45) Date of Patent: Feb. 3, 2009

(54) DOUBLE-LAYER HOLLOW MEMBRANE FOR BIO-REACTOR APPLICATIONS

(75) Inventors: Wolfgang Albrecht, Teltow (DE); Dieter Paul, Kleimachnow (DE); Roland Hilke, Teltow (DE); Barbara Seifert, Berlin (DE); Thomas Weigel, Wilhelmshorst (DE); Thomas Groth, Berlin (DE)

(73) Assignee: GKSS Forschungszentrum Geesthacht GmbH, Geesthacht (DE)

( * ) Notice: Subject to any disclaimer, the term of this patent is extended or adjusted under 35 U.S.C. 154(b) by 905 days.

(21) Appl. No.: 10/762,225

(22) Filed: Jan. 16, 2004

(65) Prior Publication Data
US 2004/0173933 A1 Sep. 9, 2004

Related U.S. Application Data

(63) Continuation-in-part of application No. PCT/DE02/02249, filed on Jun. 20, 2002.

(51) Int. Cl.
*B01D 69/12* (2006.01)
(52) U.S. Cl. .................. 264/178 R; 264/203
(58) Field of Classification Search .......... 264/178, 264/178 R, 203
See application file for complete search history.

(56) References Cited

U.S. PATENT DOCUMENTS

| | | | | | |
|---|---|---|---|---|---|
| 2,790,783 | A | * | 4/1957 | Coover, Jr. | 524/235 |
| 4,283,289 | A | * | 8/1981 | Meyst et al. | 210/448 |
| 4,973,320 | A | * | 11/1990 | Brenner et al. | 604/265 |
| 5,395,570 | A | * | 3/1995 | Kopp et al. | 264/41 |
| 5,599,380 | A | * | 2/1997 | Koros | 95/54 |
| 5,707,522 | A | * | 1/1998 | Maeda et al. | 210/500.23 |
| 5,902,745 | A | * | 5/1999 | Butler et al. | 435/297.2 |

FOREIGN PATENT DOCUMENTS

DE 4021052 * 1/1992

OTHER PUBLICATIONS

Contemporary Biomaterials, Material and Host Response, Clinical Applications, New Technology and Legal Aspects, edited by Boretos, John W. et al., Noyes Pbulications, 1984, pp. 1-17 and 180-204.*

* cited by examiner

*Primary Examiner*—Jill L Heitbrink
(74) *Attorney, Agent, or Firm*—Klaus J. Bach (57) ABSTRACT

In a method of manufacturing a double-layer membrane of different polymers or polymer mixtures with opposite blood-compatible and tissue-compatible surfaces, a first polymer solution of a blood-compatible polymer and a second solution of a tissue-compatible polymer are extruded concurrently in layered form through a nozzle into a coagulation bath so as to form a double layer membrane.

11 Claims, 10 Drawing Sheets

DOUBLE-LAYER HOLLOW MEMBRANE FOR BIO-REACTOR APPLICATIONS

This is a Continuation-in-Part application of International Application PCT/DE02/02249 filed Jun. 20, 2002 and claiming the priority of German application 101 34 447.3 filed Jul. 16, 2001.

BACKGROUND OF THE INVENTION

The invention relates to a membrane with a double-layer membrane wall whose layers consist of different polymers or, respectively, polymer mixtures and whose one surface is blood compatible whereas the other surface is tissue compatible, a method for the manufacture of this membrane and the use of this membrane as a support membrane for bio-hybrid organs.

It is already known to use membranes for the detoxification of blood outside the body during organ failure, for example during kidney failure. In this treatment, which is used today in hospitals worldwide, toxins permeate in accordance with the pore size of the dialysis membrane used and the size of the molecules of the compounds to be removed from the blood of the patient into a flushing solution, the dialysate. This process is called herein a "passive" transport which, in accordance with the laws of diffusion, is based on the difference of the concentration of the respective compounds contained in the two liquids.

In the natural kidneys, the urine toxins are in a first stage also removed by a passive process in which the primary urine is produced. However, in contrast to the artificial kidney, this passive ultra filtration process is followed by a subsequent active process, in which certain compounds of the primary urine and particularly water are returned to the blood against the concentration gradient of the primary urine. Such an active process can be established within the artificial kidney at the present state of the membrane separation technology only by vital and tissue-like organized cell layers. The same is true for other organs, for example, the pancreas and the lever. By means of porous membranes consequently only the passive filtration functions and possibly and sorptive functions of the organs responsible for detoxification can be supported or, respectively, replaced and therefore utilized for therapeutic purposes.

There were attempts to introduce the active transport of vital cells specifically for support in dysfunctions of ailing organs. The results achieved however can hardly be used for many reasons.

In view of the clinical relevance, there were also many attempts to develop suitable membrane carriers with a property profile as required for the specific application. In principle, the membrane carriers known so far can be classified in four different basic types which differ particularly in the membrane and swelling properties:

1. Highly swelling gel membranes with membrane functions (for example, ASA10 J. 39 (1993), M261-M267; Biomaterials 16 (1995) 753-759) and, respectively, porous membranes filled with gel (for example, WO 97/17129).

2. Practically not or only moderately swelling porous membranes with membrane functions in non-functionalized form (WO 95/21911, WO 96/40871, U.S. Pat. No. 5,837,234) or functionalized form (U.S. Pat. No. 5,720,969), wherein the biochemical behavior with regard to blood and tissue compatibility may be optimized with a polymer composition of the membrane former in accordance with the requirements (see DE 100 30 307.2).

3. 3D-matrix materials without separation functions (GB 2 187 447), WO 97/12960) with extremely coarse porous structure (10-100 μm).

4. Carrier materials which were manufactured by microelectronic techniques such as thin film deposition, photolithography and/or etching (for example, U.S. Pat. Nos. 5,651,900; 5,798,042; 5,893,974; 5,938,923; 5,948,255; 5,985,328).

All these developments have in common that the requirement profile of a carrier membrane for use in bio-hybrid organs is only partially fulfilled; gel membranes or gel-filled membranes have an insufficient adherence to the adhesion-dependent cells and, up to date, provide for insufficient material exchange. Non-swelling or moderately swelling membranes do not have optimal properties with regard to blood or tissue compatibility. Even an optimized polymer composition achieves only a compromise between the two characteristics. The membrane formation in accordance with a phase inversion process is often insufficient. 3D matrix materials basically do not have an immune-isolating effect which requires the use of patient cells which are not available. The permeation properties of materials manufactured by means of microelectronic techniques are insufficient and the manufacture of relatively large membrane areas is prohibitively expensive.

It is therefore the object of the present invention to provide a carrier membrane, which can be used in bio-hybrid reactors and which can be manufactured at relatively low costs.

SUMMARY OF THE INVENTION

In a method of manufacturing a double-layer membrane of different polymers or polymer mixtures with opposite blood-compatible and tissue-compatible surfaces, a first polymer solution of a blood-compatible polymer and a second solution of a tissue-compatible polymer are extruded concurrently in layered form through a nozzle into a coagulation bath so as to form a double layer membrane.

For the manufacture of the double layer membrane wall of the membrane according to the invention two chemically different polymer solutions are employed. The first polymer solution contains a blood-compatible polymer which is dissolved in a solvent. The second polymer solution is manufactured separately from the first polymer solution and contains a tissue compatible polymer. Also this tissue-compatible polymer is dissolved in a solution. The two polymer solutions are manufactured in such a way that both polymer solutions remain in the form of polymer mixture solutions in a homogeneous state.

As solvent for the manufacture of the two polymer solutions preferably the same solvent is used. But mixtures of solvents may also be used wherein, in that case, preferably at least one component of the solvent mixture employed is the same in both polymer solutions.

The two polymer mixture solutions described above which are used for the manufacture of the membrane wall are brought into contact with each other in a nozzle of an extruder while forming a layer-like polymer solution composite structure and are extruded in this form from the nozzle of the extruder as a polymer solution composite structure. The polymer solution composite structure is extruded in this process into a coagulation bath and subjected to a phase inversion. Subsequently, all non-membrane-forming components are at least partially removed from the double layer membrane formed in this way and the membrane is further treated, for example, thermally stabilized dried and packaged.

Preferably, the membrane is transported through an air space between the extrusion and the coagulation bath.

In a particularly preferred embodiment, the membrane according to the invention is in the form of a double layer hollow membrane. This is achieved in that the two polymer solutions described above are transported to the exit of the extruder nozzle together in the form of polymer mixture solutions using multi-channel hollow core nozzles as disclosed in DE 100 54 591.2, wherein the polymer solutions forming the double membrane wall are brought into contact with each other already in the extruder nozzle as they jointly leave the nozzle as a polymer solution compound structure.

Preferably, this polymer solution compound structure is stabilized at the exit of the extruder nozzle by the concurrent extrusion of a lumen filler forming the core of the hollow membrane. The membrane is then further processed as described above.

From the literature, it is known which polymers are blood-compatible or, respectively, tissue-compatible. On the basis of these literature data, the polymers can be selected in a reasonably safe way. By simple testing, it can then be determined whether the blood compatible, or respectively, tissue compatible polymer can be dissolved in the selected solvent or solvent mixture in such a way that the resulting polymer mixture solution has a homogeneous appearance. It has been found however, that copolymers form with a common co-monomer often homogeneous polymer mixture solutions. Preferably, the membrane according to the invention can therefore be obtained in that as polymer for the manufacture of the membrane wall a polymer mixture of a blood-compatible or, respectively, tissue-compatible polymer and a copolymer or, respectively, additional polymer are used. It is particularly preferable if both polymer solutions, from which the double layer membrane wall is manufactured, include, in addition to the respective blood compatible or tissue compatible polymer, also another polymer, which is the same in both polymer solutions, that is, which is chemically the same. This facilitates the manufacture of homogeneous mixture solutions. In addition, the additional common polymer can improve the compatibility and positively affect the membrane formation behavior and the behavior of the membrane under thermal stresses. It is possible in this way to provide, with the use of such poly-mixture solutions as the polymer solutions forming the membrane wall, double layer membrane walls of high structural integrity. The mass-based part of blood or, respectively, of tissue-compatible polymers and the common polymer in the total polymer content of the respective polymer solutions is preferably 10-90% and particularly preferably 40-60%.

The polymer concentration in the individual polymer solutions forming the membrane wall can be varied within wide limits and is preferably 10-30%. By varying this concentration and the extrusion conditions or, respectively, spinning conditions, the separation behavior of the double-layer membrane wall and consequently of the membrane according to the invention can be varied and, after immune isolation, adapted to the respective type of cells in corresponding bio-hybrid systems. These polymers are dissolved in solvents or, respectively mixtures of solvents which are known to a person skilled in the art for use in connection with the polymers.

Below the invention will be described in connection with hollow membranes, which is done only because it is easier to show and explain. But the measures described can also be used accordingly or in an analogous manner in connection with flat membranes.

For the manufacture of the membrane according to the invention in the form of a hollow membrane, the two polymer solutions forming the membrane wall are joined using the multi-channel hollow core nozzle described in DE 100 54 591.2 already in the deformation device to a layered polymer structure which is extruded out of the extrusion nozzle as a polymer solution structure. At the exit of the nozzle, the polymer structure is stabilized by a concurrent extrusion of a lumen filler and moved under given conditions through an airspace into a medium which has a coagulating effect on the formed-out polymer solutions. In this medium, the polymer solution structure is solidified as a double-layer hollow fiber membrane by phase inversion.

The further procedure corresponds to the hollow fiber manufacturing process as it is known to the person skilled in the art wherein the hollow membrane may be stretched, is washed and possibly thermally stabilized and conditioned and finally dried and packaged.

In contrast to the single-layer membrane in the possibly needed stabilizing step of a double layer hollow membrane, the temperatures for the stabilization have to be so selected that the temperature is lower than the glass conversion point of that polymer layer, which has the lower glass conversion point. Advantageous also in this case is the addition of a common polymer in both polymer solutions, which has a glass conversion point that is higher than the glass conversion points of the blood- and the tissue-compatible polymer.

Characteristic for the double-layer membrane according to the invention is consequently on one hand a bi-functional chemical structure to which a structurally symmetrical arrangement may be superimposed and, on the other hand, a structural integrity of the polymer layers which form the double-layer membrane wall (adherence of the two polymer layers).

The porous membrane according to the invention, particularly in the form of a porous hollow membrane, can be used preferably as a carrier membrane in bio-hybrid organs (hybrids of passive membrane functions and active organ cell function) for the support or, respectively, the temporary replacement of damaged organs.

The porous membrane according to the invention is on one hand—in accordance with the intended use—sufficiently permeable but also, on the other hand, immuno-isolating and is blood- as well as tissue-compatible. In addition, it has an exactly controllable protein absorption behavior and can be manufactured at low costs.

In accordance with a preferred embodiment, a hollow membrane according to the invention has an inner surface which is blood-compatible and an opposite outer surface which is tissue-compatible.

Both membrane layers of the hollow membrane cross-section have structural integrity providing for an adherence of the two layers to form the composite membrane. This condition facilitates on one hand a long-term vitality and -function of the generally adhesion-dependent cells and their arrangement and tissue structure, which organize themselves in a polarized manner and, on the other hand, provides for a long term blood compatibility which is needed for the use of bio-hybrid systems. By varying the manufacturing conditions, the separation properties of the double-layer hollow membranes can be obtained such that an organ-specific immune isolation can be obtained and available allogenic or respectively, xenogenic cells can be inserted into a bio-hybrid organ without activation of the immune system of a patient. Consequently, patient cells are no longer needed in order to prevent, upon introduction of bio-hybrid systems, an activation of the immune defense of the human body against the bio-hybrid organ. In summary, hollow membrane organs are provided which comply with the complex requirement profile for the use of carrier membranes in bio-hybrid systems.

Below the invention will be described in greater detail on the basis of preferred embodiments with reference to the accompanying drawings.

DESCRIPTION OF EXAMPLES

The manufacture of double-layer porous hollow membranes of different acrylnitrile polymers and their characteristics are described. In addition, the use of this hollow membrane in accordance with the invention as carrier membrane in bio-hybrid systems with the use of kidney epithelial cells (MDCH-cells) is described. As acrylnitrile polymers the following polymers with the following properties were used:

| product | Co-monomer | content [Mol %] | property | Location of layer | manu-facturer |
|---|---|---|---|---|---|
| PAN* | without | — | Reinforcing stabilizing | Addition inside and/or outside | Hoechst |
| ANNVP5 | NVP** | 6.1 | Tissue compatible | Outside | Lab-product |

-continued

| product | Co-monomer | content [Mol %] | property | Location of layer | manu-facturer |
|---|---|---|---|---|---|
| ANNVP20 | NVP** | 18.0 | Blood compatible | Inside | Lab-product |
| ANAPMA | APMA*** | 3.8 | Functionalizable | inside | Lab-product |

*polyacrylnitrite
**N-vinyl pyrrolidon
***amino propylmethacrylamide

The good blood compatibility of the ANNVP 20—copolymer used herein is described and documented in DE 100 30 307.2. The excellent tissue compatiblity of polyacrylnitril and its copolymers ANNVP5 for kidney epithelial cells is documented in the publication "Morphological studies on the culture of kidney epithelial cells in a fiber-in-fiber bio-reactor design using hollow fiber membranes* (F. Fey Lambrecht, W. Albrecht, Th. Groth, Th. Weigel, V. Gross, J. Biomed. Mat. Res).(entered 2001).

Example 1

Figure 1:
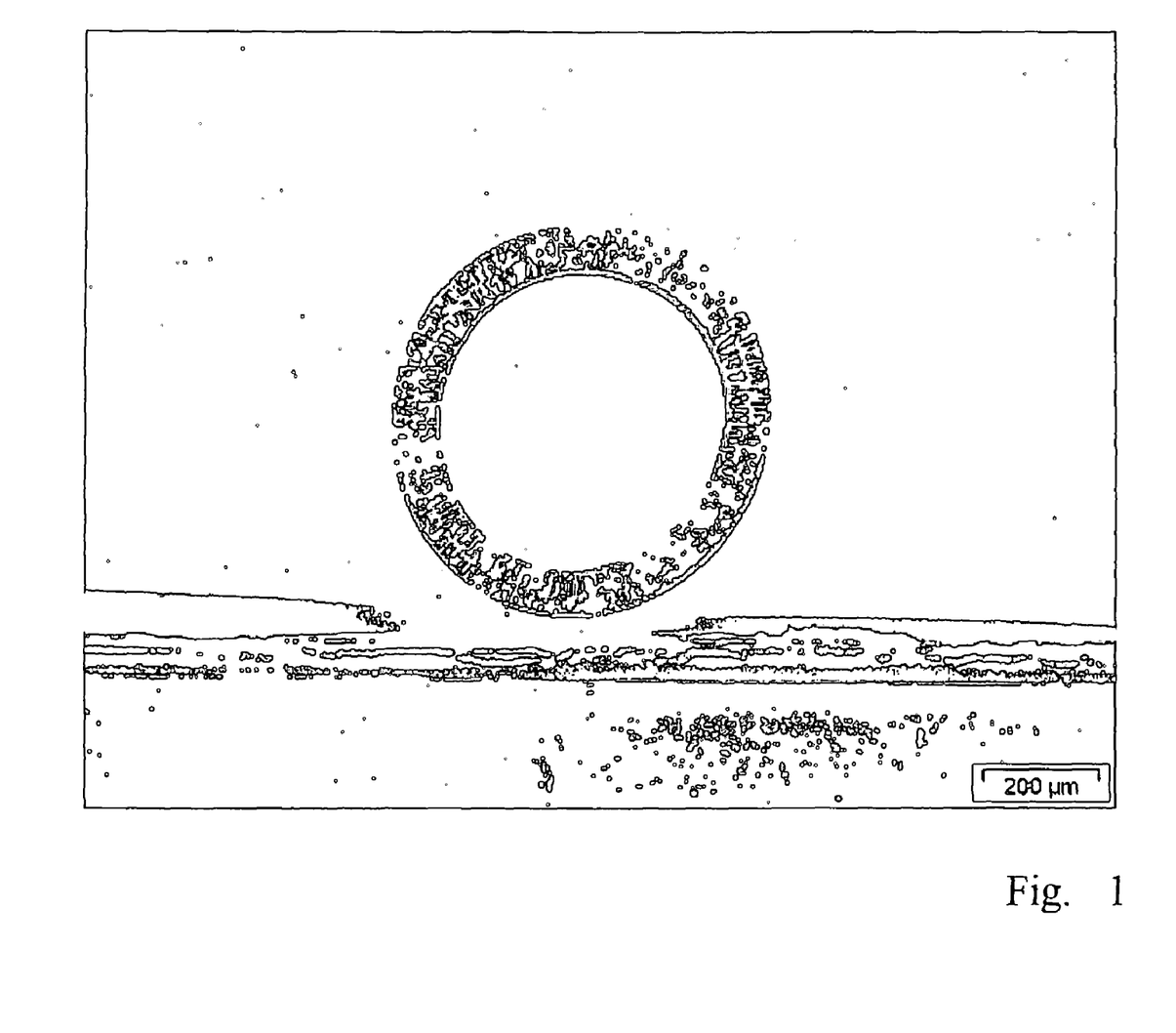
FIG. 1 shows a raster-electron microscopic representation of the cross-section of the double-layer hollow membrane in accordance with the example 1.
Figure 2:
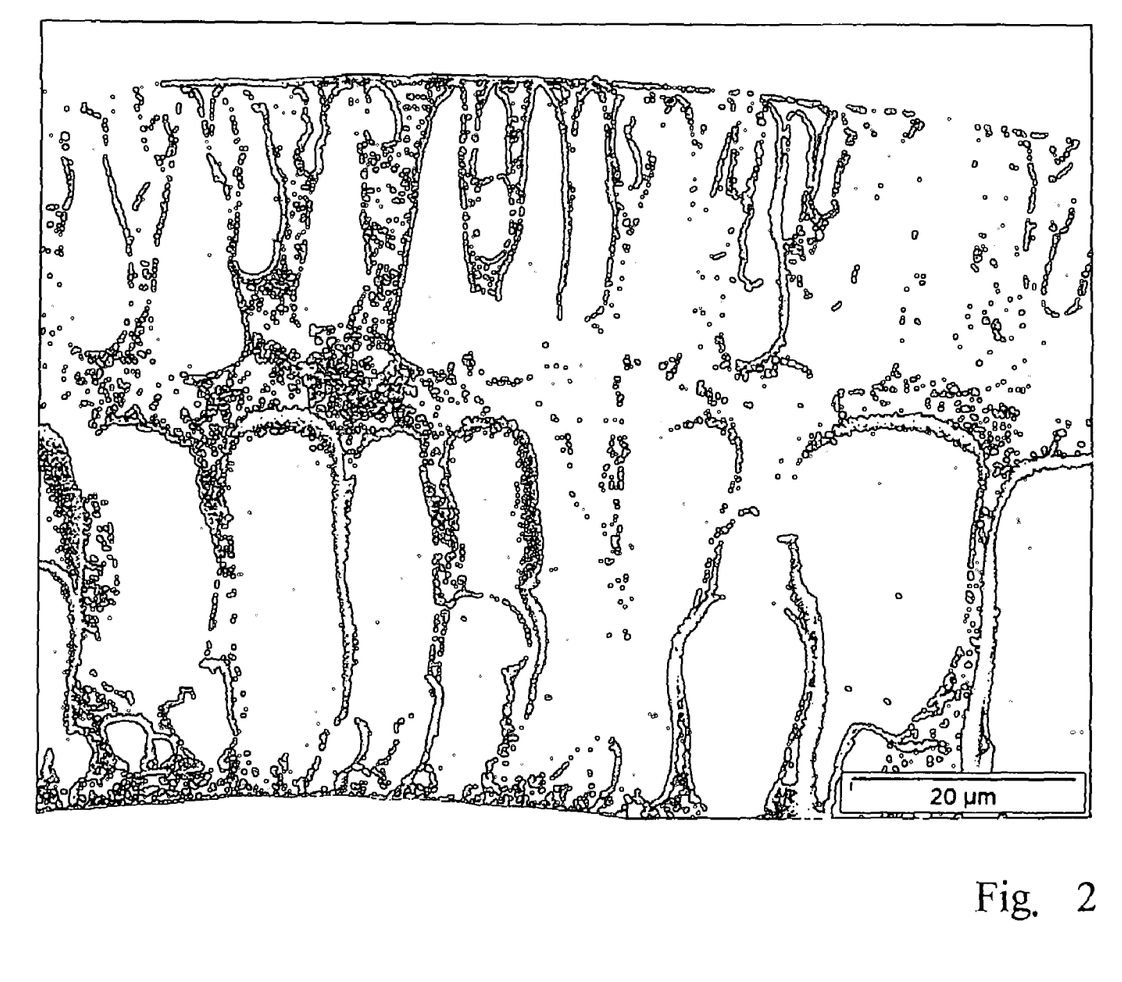
FIG. 2 shows a raster-electron microscopic representation of the cross-section of the double layer hollow membrane according to example 1, highly amplified.

A polymer consisting of 8 parts PAN, 8 parts ANNVP 5-copolymer and 84 parts N,N-diemthylformamide (DMF) was prepared by dissolving the polymers and stirring for 2 hrs at 80° C., wherein, in a first stage, the PAN was dissolved in the solvent and the appropriate amount of AN-copolymer was added. After cooling, this polymer solution was filtered, degasified using a filter combination consisting of polyester separator (Sartorius)/fleece (Carl Freudenberg) and was then used as polymer mixture solution for the outer membrane layer of the double layer membrane. In the same way, a solution consisting of 8 parts PAN, 9 parts ANNVP 20-copolymer and 84 parts DMF was made, prepared and used as polymer mixture solution for the inner polymer layer. As lumen filler and as coagulation bath water was used. The polymer mixture solutions were combined using a multi-channel hollow core nozzle with the dimensions 190 μm/360 μm/560 μm/760 μm/(narrow pin diameter) inner slot diameter/diameter of the combining structure of the two polymer mixture solutions in the nozzle/outer slot diameter) to form a stabilized polymer solution compound, and extruded directly into a coagulation bath. Under the influence of the lumen filler and the coagulation bath the polymer solution compound is fixed and is pulled off at a speed of 8 m/min at the end of the coagulation bath, is washed by means of a washing drum and wound onto coils. In this way, a discontinuous washing occurs for more than 12 hrs. Subsequently, the double layer hollow membrane was continuously stabilized thermally at 98° C. for about 5 sec., fixed at 4° C. for about 3 sec. treated with 15 wt % aqueous glycerol solution, wound onto a spool and dried at room temperature. A double layer hollow membrane was obtained whose morphology is represented in FIGS. 1 and 2.

The double hollow membrane according to the invention formed had a structural integrity over the membrane cross-section composed of a blood-compatible inner layer and a tissue-compatible outer layer. Both polymer layers are fully joined to each other. In spite of a large magnification, no interface area between the two polymer layers could be recognized in the pictures taken by a raster electron microscope. The different form and structure of the finger pores which are the result of the different phase inversion of the two polymer solutions however shows that there is a double layer structure in the membrane cross-section. The ratio of the two polymer layers of the double layer membrane with regard to the layer thickness is about 1.

Further characteristic data of this hollow membrane are presented below:

| | |
|---|---|
| Inner diameter [μm]: | 508 |
| Total wall thickness [μm]: | 78 |
| Water permeability [lm$^{-2}$h$^{-1}$kPa$^{-1}$]: | 0.05 |

Example 2

As in the Example 1 a double layer hollow membrane was prepared with the difference that it was thermally stabilized at 30° C.

Figure 3:
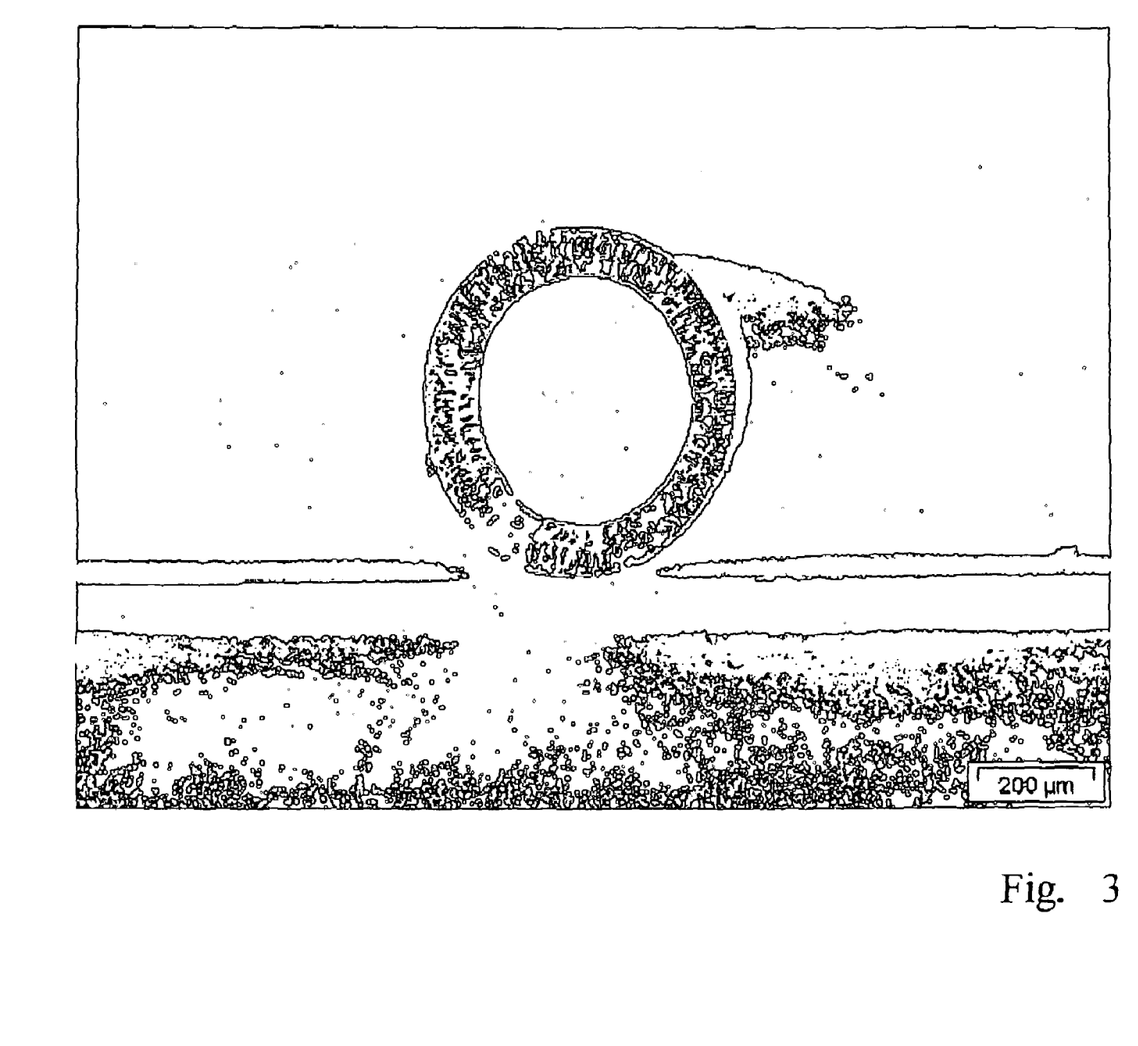
FIG. 3 shows a raster electron microscopic representation of the cross-section of the double layer hollow membrane in accordance with example 2.
Figure 4:
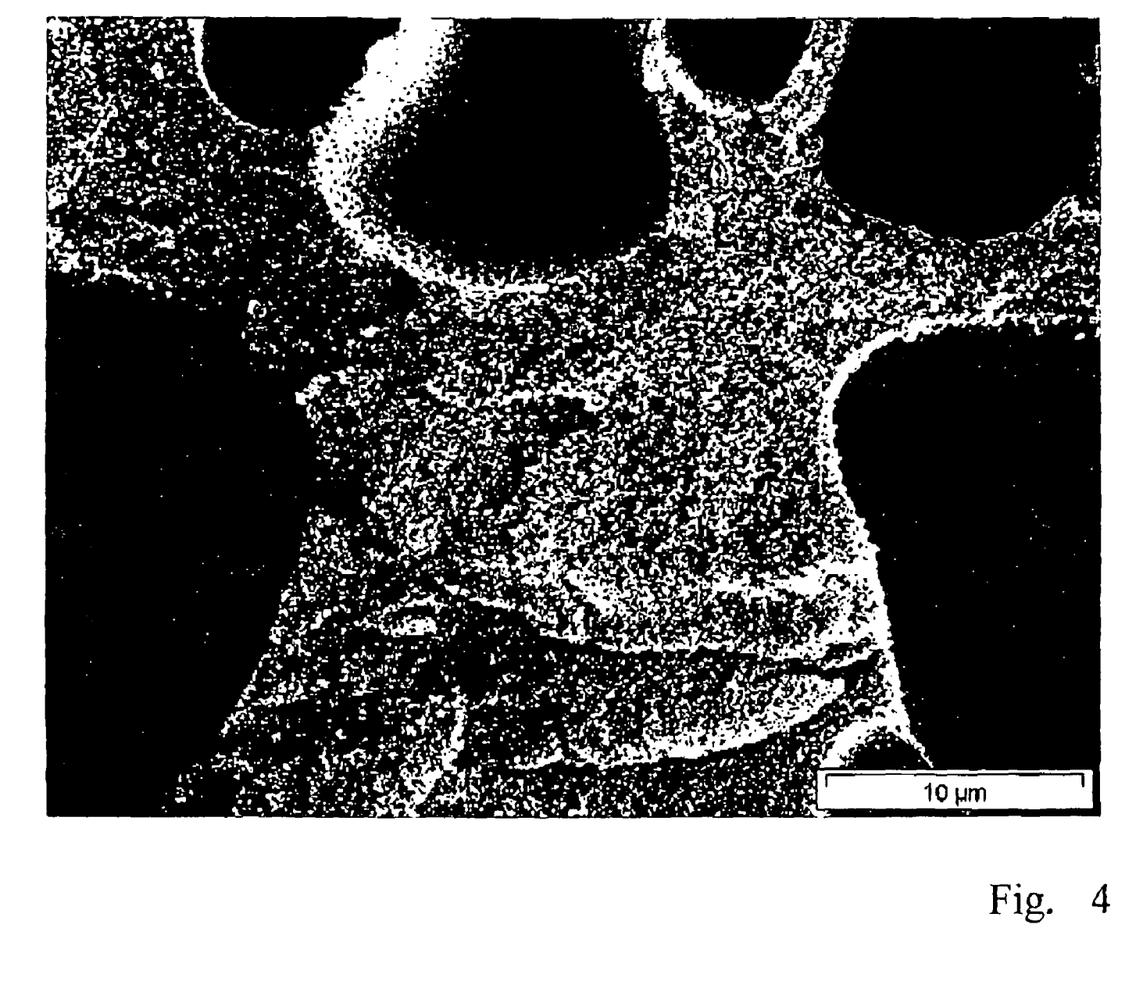
FIG. 4 shows a raster electron microscopic picture of the interface layer between the two polymer layers of the double layer membrane according to the example 2.

The morphology of this double layer hollow membrane is shown in FIG. 3 and a highly enlarged picture of the interface layer between the two polymer layers of this membrane is presented in FIG. 4.

A double layer hollow membrane in the context of the present invention was formed with a structural integrity over the membrane cross-section consisting of a blood-compatible inner layer and a tissue-compatible outer layer. In FIG. 4, the interface layer between the two layers is indicated. The structural integrity of the cross-section is so ideal that the presence of the interface layer can be assumed in the lower part of FIG. 4 only from little changes in the morphology. The total structure however shows clearly the structure of the double layer hollow fiber membrane consisting of two polymer layers. The ratio of the two layer thicknesses is about 1.

Further characteristic data of this hollow membrane are presented below:

| | |
|---|---|
| Inner diameter [μm]: | 405 |
| Total wall thickness [μm]: | 87 |
| Water permeability [lm$^{-2}$h$^{-1}$kPa$^{-1}$]: | 0.43 |
| Average pore diameter [nm]: | 5.6 |
| Cut-off [kDa]: | 38.0 |

Example 3

A double layer hollow membrane was prepared like in example 2 with the difference that the polymer solution which, in the double layer hollow membrane, forms the inner membrane consisted of 16 parts ANAPMA and 84 parts of DMF.

Figure 5:
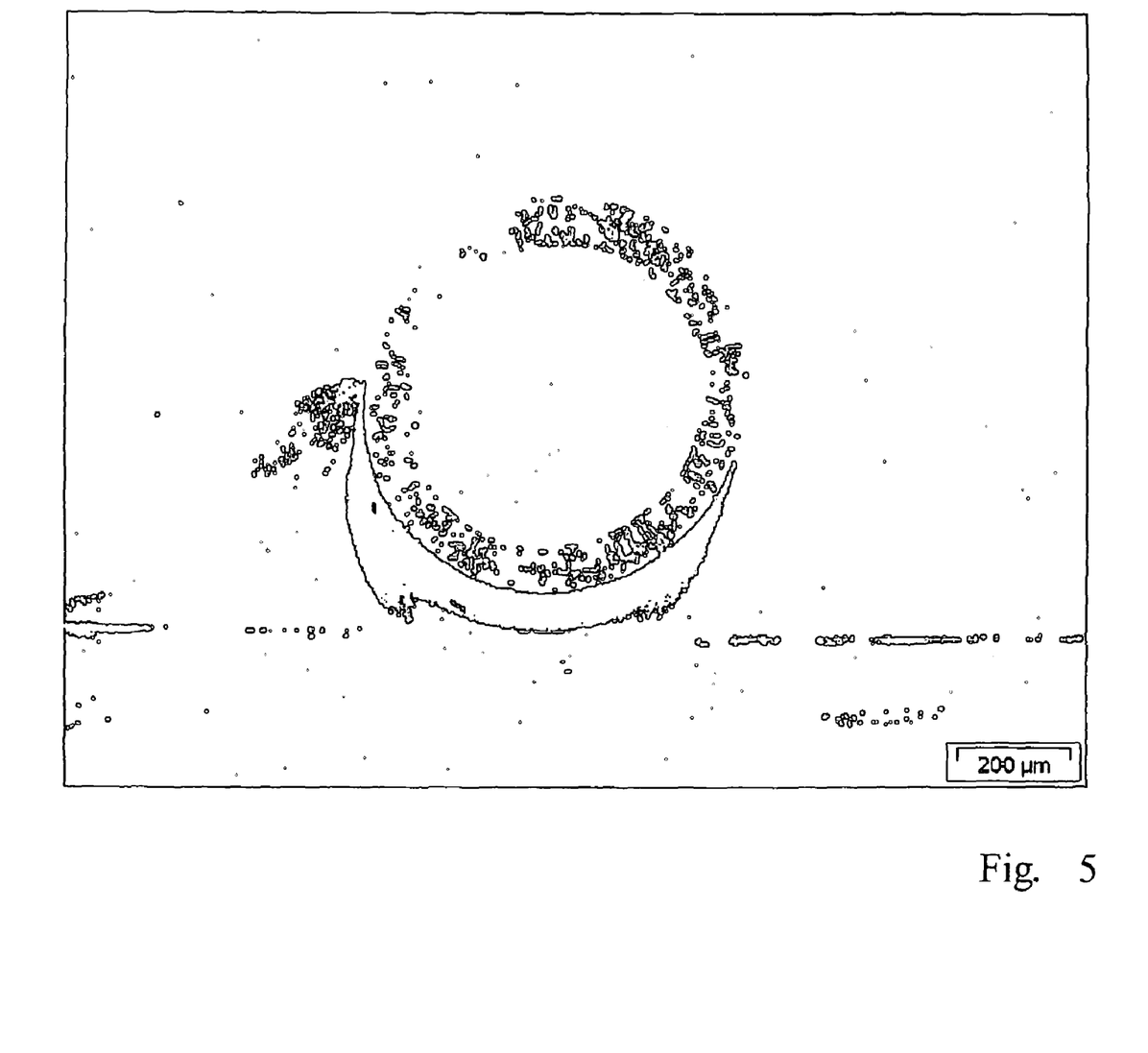
FIG. 5 shows a raster electron microscopic picture of the cross-section of the double layer hollow membrane according to example 3.
Figure 6:
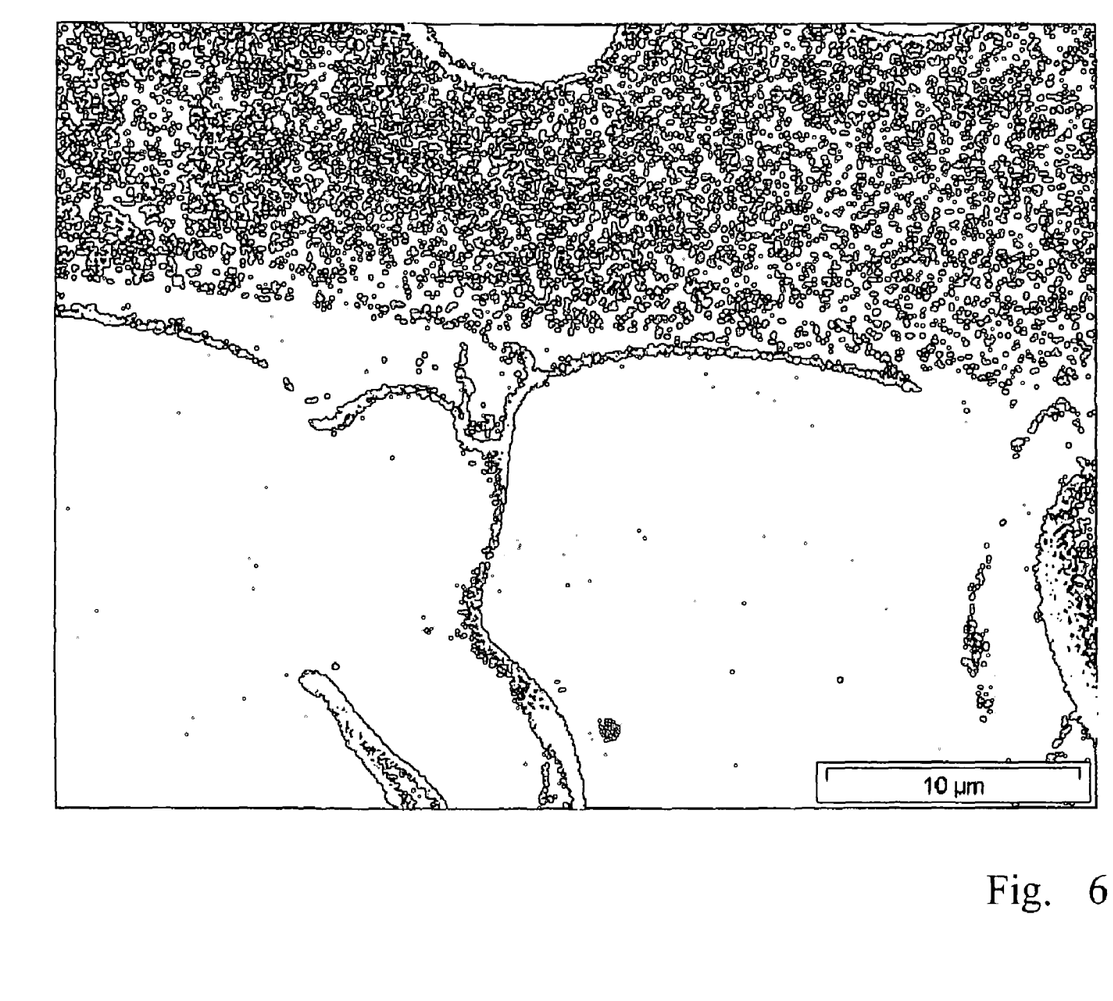
FIG. 6 shows a raster electron microscopic picture of the interface layer between two polymer layers of the double layer hollow membrane according to example 3.

The morphology of this double layer hollow membrane is shown in FIG. 5 and that of the interface area between the two polymer layers of this double layer- hollow membrane is represented in FIG. 6.

A double layer hollow membrane was formed in accordance with the invention with an amino group-containing inner layer, which can be functionalized with heparin so as to be well blood compatible and with a tissue compatible outer layer. FIG. 5 shows the high structural integrity between the two polymer layers. In FIG. 6, the interface between the two polymer layers can be clearly identified by clearly differentiated structural distinctions. Again a practically ideal structural integrity of the two polymer layers of the membrane cross-section is obtained.

Further characteristic data of this hollow membrane are presented below:

| | |
|---|---|
| Inner diameter [μm]: | 530 |
| Total wall thickness [μm]: | 76 |
| Water permeability [lm$^{-2}$h$^{-1}$kPa$^{-1}$]: | 0.70 |
| Average pore diameter [nm]: | 6.4 |
| Cut-off [kDa]: | 42.7 |

The presence of amino groups in polymer materials can be determined qualitatively by colorization with trinitrobenzene sulfate (TMBS-assay, color change from white to yellow) as is known to a person skilled in the art. With the use of this color test the color of the inner layer of the two-layer hollow membrane changed in the example 3 from white to yellow-orange which qualitatively indicates the presence of amino functions. At the same time, the intense color change from white to yellow-orange indicates that the free available amino groups are reactive in an aqueous environment, that is, that they are suitable for a heparinization. Free amino groups can be functionalized with heparin as is known to the person skilled in the art which results in an improved blood compatibility of the polymers (for example: K. G. Al-Lamee, Y. Taktak: New methods for surface modification and covalent attachment of heparin. Med. Device Technol. 9 (1998): 24-27; W. Marconi, F. Benvenuti, A.Piozzi: Covalent bonding of heparin to a vinyl copolymer for biomedical applications. Biomaterials 18 (1997): 885-890; C. H. Bamford, K. G., Al-Lamee: Chemical methods for improving the biocompatiblity of synthetic polymers. Clin. Mater. 10(1992): 243-261).

For heparinization, the two-layer membranes of example 3 were immersed at room temperature into a solution which contained 10 mg/ml heparin and a coupling agent in the mole ratio 40:1 based on heparin. The heparinized and intensively water-washed double layer hollow membrane was subsequently colored by toluidin blue; whereby the color of the inner polymer layer of this double layer hollow membrane changed from white to dark blue which qualitatively indicates large amounts of bonded heparin.

Example 4

(Application Example)

MDCK cells were cultivated for up to 8 days in a fiber-in-fiber bioreactor (see EP 1 090 984) between two chemically different hollow fibers. The outer fiber consisted of hydrophilized polysulfon (small tissue compatibility) with an inner diamater of 818 nm. As inner fiber, an ANNVP5 hollow fiber was used, whose tissue compatibility is comparable with the double layer hollow fiber described in example 2 (50% content of this polymer in the outer layer).

Figure 7:
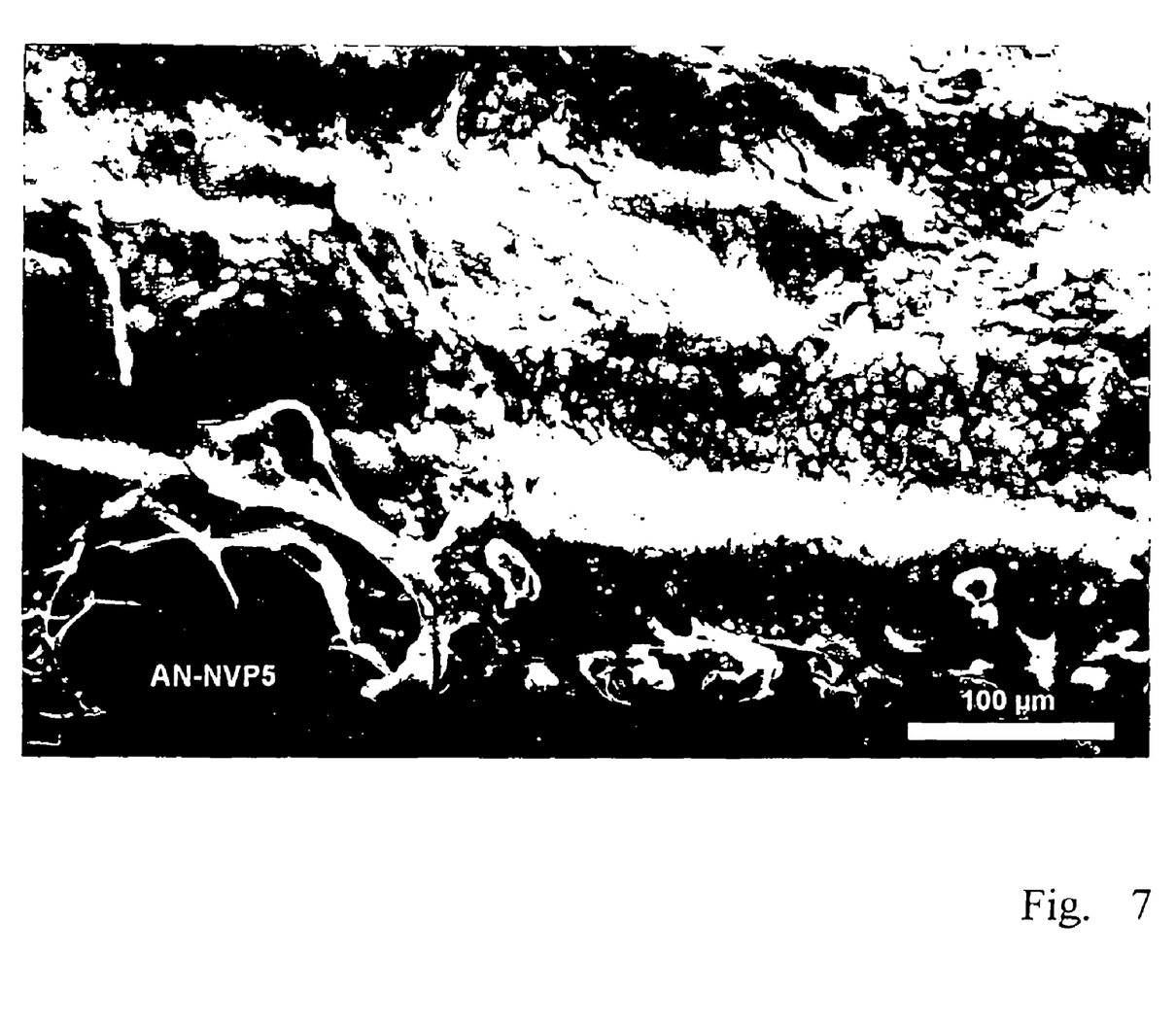
FIG. 7 shows a raster electron microscopic picture of MCDK cells, which were cultivated for 8 days in a fiber-in-fiber bio-reactor between an outer polysulfon fiber and an inner ANNVP5-fiber.
Figure 8:
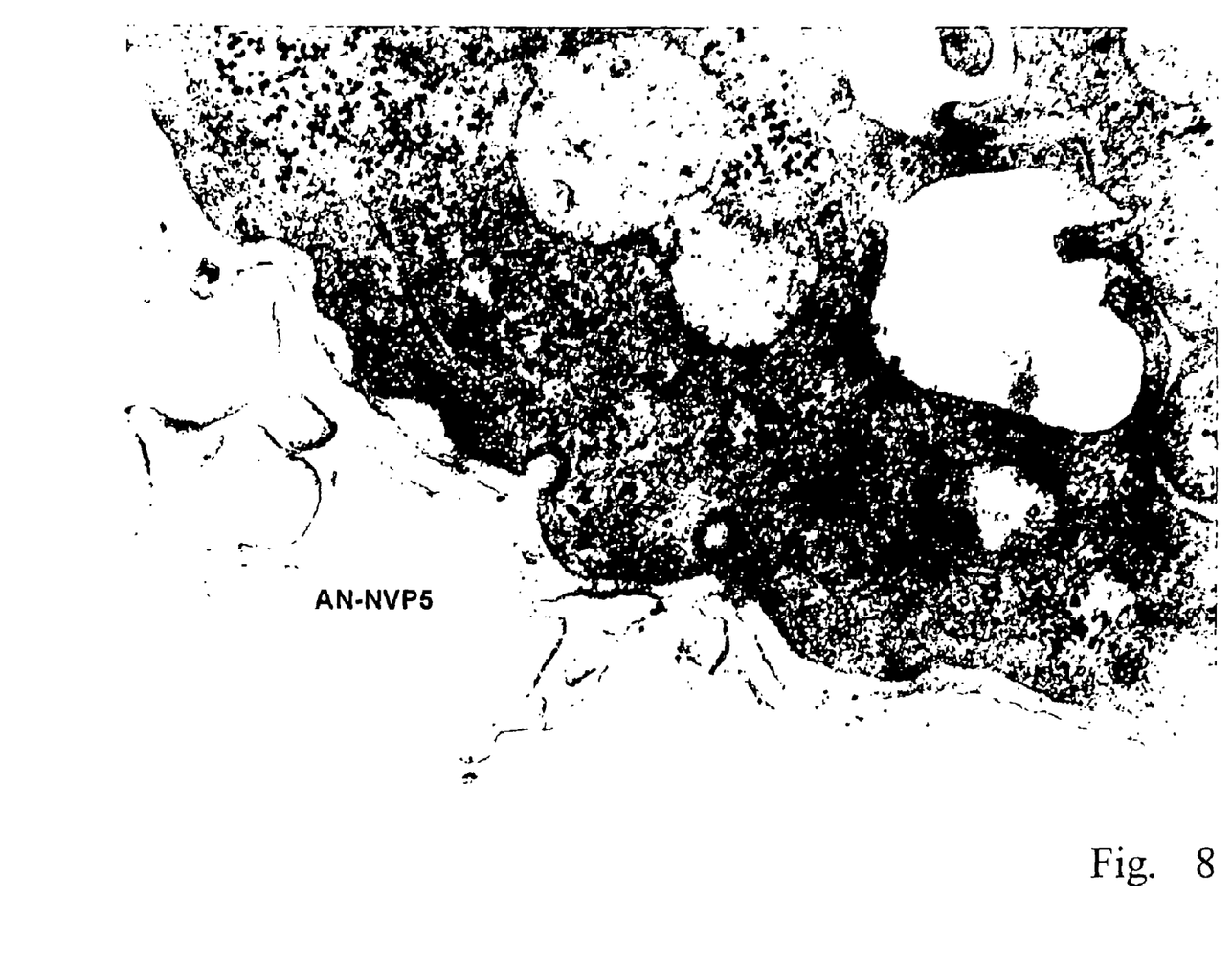
FIG. 8 shows a transmission-electron microscopic picture of MDCK cells, which were cultivated for 8 days in a fiber-in-fiber bioreactor between an outer polysulfon fiber and an inner ANNVP5 fiber; the tight cell contact to the ANNVP5 fiber is clearly visible (magnification: 21,000 times)
Figure 9:
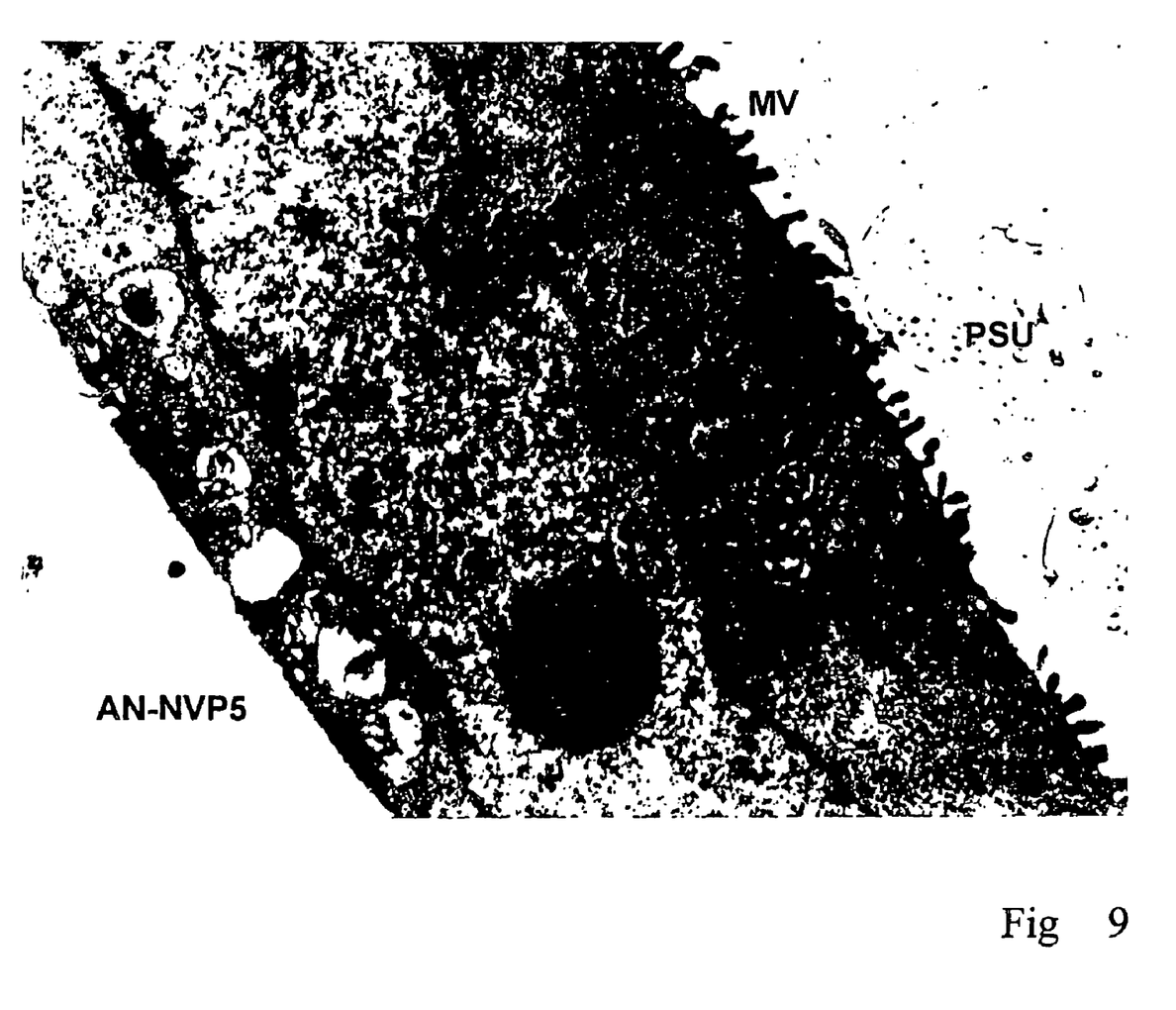
FIG. 9 shows a transmission electron microscopic picture of MDCK cells, which were cultivated for 7 days in a fiber-in-fiber bioreactor between an outer polysulfon fiber and an inner ANNVP5-fiber and numerous microvillosities (MV) are apparent (magnification; 7,100 times)
Figure 10:
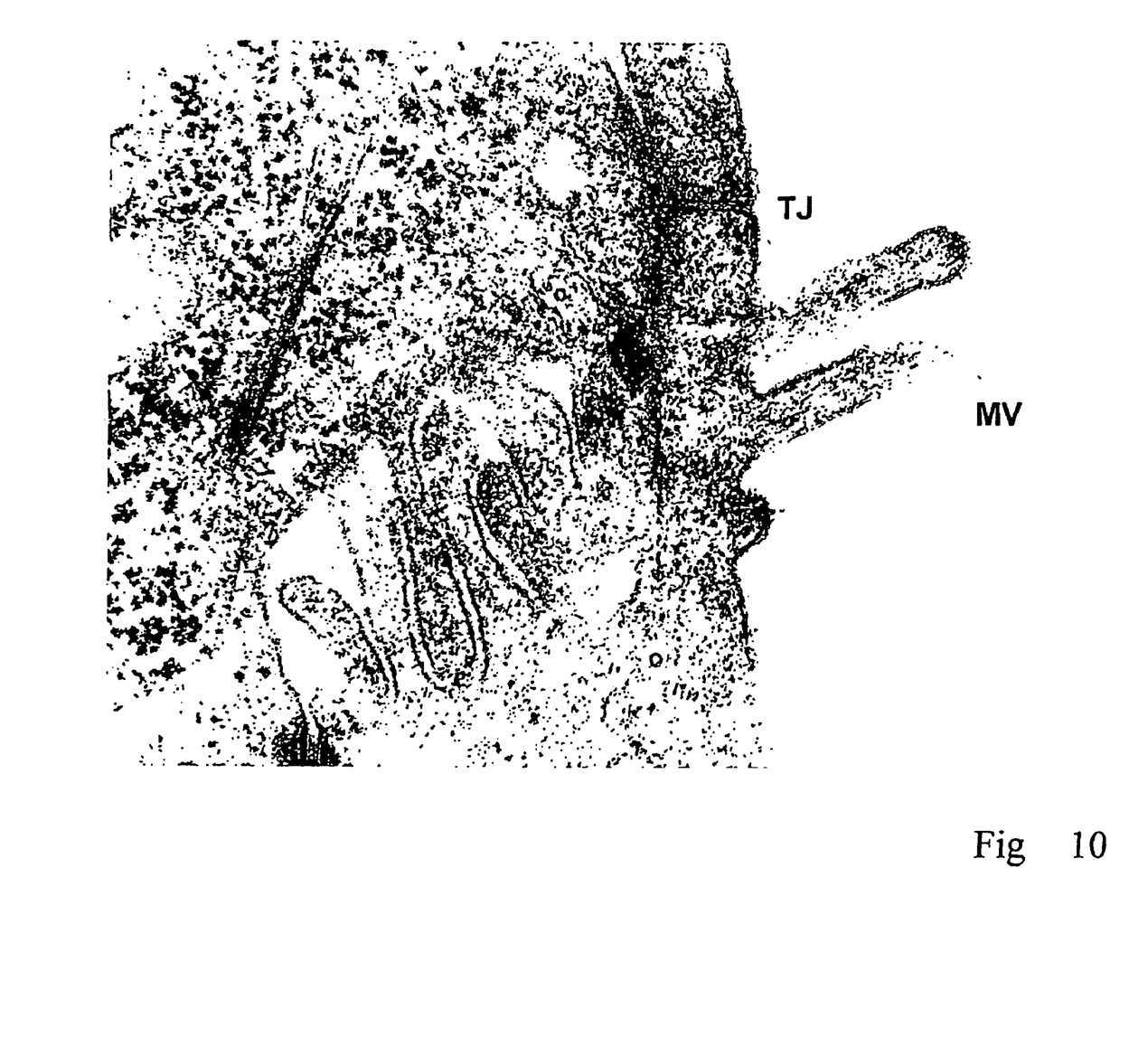
FIG. 10 shows a transmission electron microscopic picture of MDCK-cells which were cultivated for 7 days in a fiber-in-fiber bioreactor between an outer polysulfon fiber and an inner ANNVP5-fiber; clearly visible are the good contact (tight junctions—TJ) and the formation of the microvillosities (MV; magnification; 31,000 times).

The results indicate that the MDCK cells adhere preferably to the inner fiber and form there after 8 days a confluent layer of uniform hexagonal cells which have the MDCK-typical morphology (FIG. 7) TEM pictures show a close contact of the cells with the ANNVP5 fiber (FIG. 8). Numerous microvillosities (MV, FIG. 9) as well as cell-cell contacts (tight junctions—T.J. FIG. 10) are visible and well developed. These findings indicate a functional epithelial, which confirms the high compatibility of the membrane surface with kidney epithelial cells.

What is claimed is:

1. A method of manufacturing a membrane with a double layer membrane wall whose layers consist of different polyacrylnitrile copolymers so that the layer forming one surface of the double layer membrane is blood-compatible whereas the layer forming the other surface of the double layer membrane is tissue-compatible, said method comprising the steps of:

preparing, separately, a first polymer solution which contains a blood-compatible polymer comprising at least one of polyacrylnitrile copolymer P(AN-co-NVP) with a fraction of NVP between 18.0 and 20.9 mol-%, heparinized polyacrynitrile copolymer P(AN-co-APMA) with a fraction of 3.8 mol-% APMA, a mixture thereof and a mixture of at least one of polyacrylnitrile copolymer P(AN-co-NVP) with a fraction of NVP between 18.0 and 20.9 mol-% and heparinized polyacrylnitrile copolymer P(AN-co-APMA) with a fraction of 3.8 mol-% APMA with polyacrylnitrile,     and a second polymer solution which contains a tissue-compatible polymer comprising at least one of polyacrylnitrile copolymer P(AN-co-NVP) with a fraction of NVP between 4.8 and 6.1 mol %, and a mixture thereof with polyacrylnitrile by dissolving the respective polymer in a solvent such that both polymer solutions remain in the form of polymer mixture solutions in a homogeneous state,     bringing the two polymer solutions into contact with each other in the nozzle of an extruder so as to form a layered polymer solution compound arrangement,     and extruding the two polymer solution compound arrangement from the nozzle of the extruder into a coagulation bath where it is subject to a phase inversion thereby forming a double layer membrane with a blood-compatible material surface at one side thereof and a tissue-compatible surface at the other side thereof which is at least partially freed from all non-membrane forming components.

2. A method of manufacturing a membrane according to claim 1, wherein, before the extrusion into the coagulation bath, the membrane is passed through an air space.

3. A method of manufacturing a membrane according to claim 1, in the form of a double layer hollow membrane, wherein as extruder a spin extrusion nozzle is used.

4. A method of manufacturing a membrane according to claim 3, wherein as an extruder nozzle a multi-channel hollow core nozzle is used.

5. A method of manufacturing a membrane according to claim 3, wherein the polymer solution compound arrangement at the exit of the extrusion nozzle is stabilized in its form by the concurrent extrusion of a lumen filler forming the hollow core.

6. A method of manufacturing a membrane according to claim 3, wherein the polymer material forming the inner surface of the hollow membrane is blood-compatible and the polymer forming the outer surface is tissue-compatible.

7. A method of manufacturing a membrane according to claim 1, wherein a first and a second polymer solution are used which both include the same solvent.

8. A method of manufacturing a membrane according to claim 1, wherein a first and a second polymer solution are used which include an additional polymer which is the same in both polymer solutions.

9. A method of manufacturing a membrane according to claim 8, wherein the mass content of blood-compatible and, respectively, tissuecompatible polymers and the additional polymer in the total polymer content of the respective polymer solution is 10 to 90%.

10. A method of manufacturing a membrane according to claim 1, wherein the concentration of the polymer in the first and second polymer solutions each is 10 to 30%.

11. A method according to claim 8, wherein the mass content of blood-compatible and, respectively, tissue compatible polymers and the additional polymers in the total polymer content of the respective polymer solution is 40 to 50%.

\* \* \* \* \*